(12) United States Patent
Lebovic

(10) Patent No.: US 6,309,369 B1
(45) Date of Patent: *Oct. 30, 2001

(54) SURGICAL BINDER AND METHODS OF USE

(76) Inventor: Gail S. Lebovic, 1204 Sharon Park Dr., No. 79, Menlo Park, CA (US) 94025

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/083,517

(22) Filed: May 22, 1998

(51) Int. Cl.[7] ........................................ A61F 13/00
(52) U.S. Cl. ................................ 602/75; 602/19
(58) Field of Search ................... 602/60, 61, 62, 602/63, 74, 75, 78, 79; 2/463, 464, 913, 73, 67, 69, 110; 450/31, 32, 33, 52, 53–57

(56) References Cited

U.S. PATENT DOCUMENTS

| 3,194,234 | 7/1965 | Duckman et al. . |
|---|---|---|
| 3,442,270 | 5/1969 | Steinman . |
| 3,968,803 | 7/1976 | Hyman . |
| 5,045,018 | * 9/1991 | Costanzo ........................... 450/31 |
| 5,137,508 | 8/1992 | Engman . |
| 5,152,741 | 10/1992 | Farnio . |
| 5,158,541 | 10/1992 | McCurley . |
| 5,429,593 | 7/1995 | Matory . |
| 5,456,660 | 10/1995 | Reich et al. . |
| 5,527,270 | 6/1996 | Chase et al. . |
| 5,538,502 | 7/1996 | Johnstone . |

OTHER PUBLICATIONS

K. Ruddy, "Random Shirring on a Dress Bodice," *Notions*, American Sewing Guild, pp. 8–9, 20–21 (Jan. 1997).

* cited by examiner

Primary Examiner—Kim M. Lewis
(74) *Attorney, Agent, or Firm*—Mueting, Raasch & Gebhardt, P.A.

(57) ABSTRACT

A binder for application of pressure to the wound area of a patient who has undergone a mastectomy or other type of chest surgery. The binder includes an elasticized main body portion formed from a fabric that is substantially nonelastic, yet breathable, with gathering, elastic stitching therein.

10 Claims, 2 Drawing Sheets

SURGICAL BINDER AND METHODS OF USE

BACKGROUND OF THE INVENTION

The present invention relates to a binder for use after surgery, and more particularly, to a binder for securing a bandage or dressing over the torso, particularly the chest area, of a person. After a surgical breast procedure, such as a mastectomy, or other chest surgery, it is necessary for the patient to wear a bandage or dressing over the wound area, which is typically changed once per day. Because this dressing is typically required for several weeks, the patient may need to change the dressing without assistance. Thus, it is desirable that the means used to secure the dressing be easy to put on and take off. It is also desirable that the means used to secure the dressing be comfortable, without significantly chafing the skin or trapping moisture against the skin, and easily adjustable to achieve proper fit.

One means of securing a dressing involves the use of nonadhesive bandages that encircle the chest of a patient. Such bandages typically are made of an elastic material for even distribution of pressure. Although some elastic materials breathe to a limited extent, they tend to entrap significantly more moisture against the skin as compared to a breathable material such as cotton, gauze, flannel, or other fabrics.

U.S. Pat. No. 5,527,270 (Chase et al.) describes a bandage that includes a main body panel formed of a nonelastic, breathable material. The main body panel is configured to encircle the torso of a person, the ends of the main body panel being located adjacent one side of the person's body when the bandage is applied. An elastic member is attached at one side of the nonelastic main body panel. When the bandage is applied, the main body panel is wrapped around the chest of the person and secured on the side of the person's body on which surgery was not performed (assuming the person has undergone only a single mastectomy). However, such a bandage does not typically evenly distribute the pressure.

What is needed is a surgical binder that is breathable and generally easy to apply and remove, and is preferably capable of evenly distributing pressure.

SUMMARY OF THE INVENTION

The present invention provides a surgical binder that overlies a wound dressing or bandage and serves to hold them in place. The surgical binder includes a main body portion that is made of a breathable material at least a portion of which is elasticized using gathering, elastic stitching. Preferably, prior to elasticizing, the breathable material is substantially nonelastic (i.e., substantially nonstretchable). More preferably, the gathering, elastic stitching is substantially uniformly distributed over the entire surface of the material forming the main body portion. This allows for the application of evenly distributed pressure for gentle but firm compression to a wound. Significantly, the binder provides increased comfort with decreased bruising and swelling. Preferred embodiments of the binder do not significantly chafe the skin or trap a substantial amount of moisture against the skin. Moreover, the binder has an elegant yet inexpensive construction, which can be quite attractive and nonmedical-looking.

The binder of the present invention can be used on a patient who has undergone a mastectomy, breast biopsy, breast reduction, breast enlargement, reconstruction, implantation, or other type of chest surgery. It should be understood, however, that the present invention is not limited to such use but may be employed to apply pressure over other types of wounds and to other areas of the body, such as the abdomen, for example.

The binder comprises an elasticized main body portion formed of breathable material with gathering, elastic stitching (often referred to as shirring) therein, and a fastening system attached to the main body portion. The main body portion is configured to encircle the torso of a patient. Typically, the elasticized main body portion is elongated with an inner side (i.e., that which is in contact with the patient), an outer side, two opposing edges, and two opposing ends. The fastener system is preferably attached to the ends of the main body portion. When the binder is applied, the elasticized main body portion is wrapped around the chest of the patient and secured. The ends of the elasticized main body portion can form a closure located at any location on the torso of a patient. For example, it can be either at the front or adjacent one side of the patient's body, which enables the patient to apply and remove the binder. Alternatively, the binder can be configured to be closed at the back of the patient's body. Optionally, at least one strap can be attached to the elasticized main body portion to hold the binder in place.

The fastener system preferably includes a hook and loop fastener. This fastener allows a wide range of adjustability to accommodate variations in swelling and is easy to manipulate. Typically, the hook and loop fastener is attached at the ends of the main body portion such that half of the fastener (e.g., the hook portion) is attached at one end on the inner side of the main body portion and the other half (e.g., the loop portion) is attached at the other end on the outer side of the elasticized main body portion. When the binder is applied, the inner side of one end of the elasticized main body portion overlaps the outer side of the other end of the elasticized main body portion.

DETAILED DESCRIPTION OF THE PREFERRED EMBODIMENTS

Figure 1:
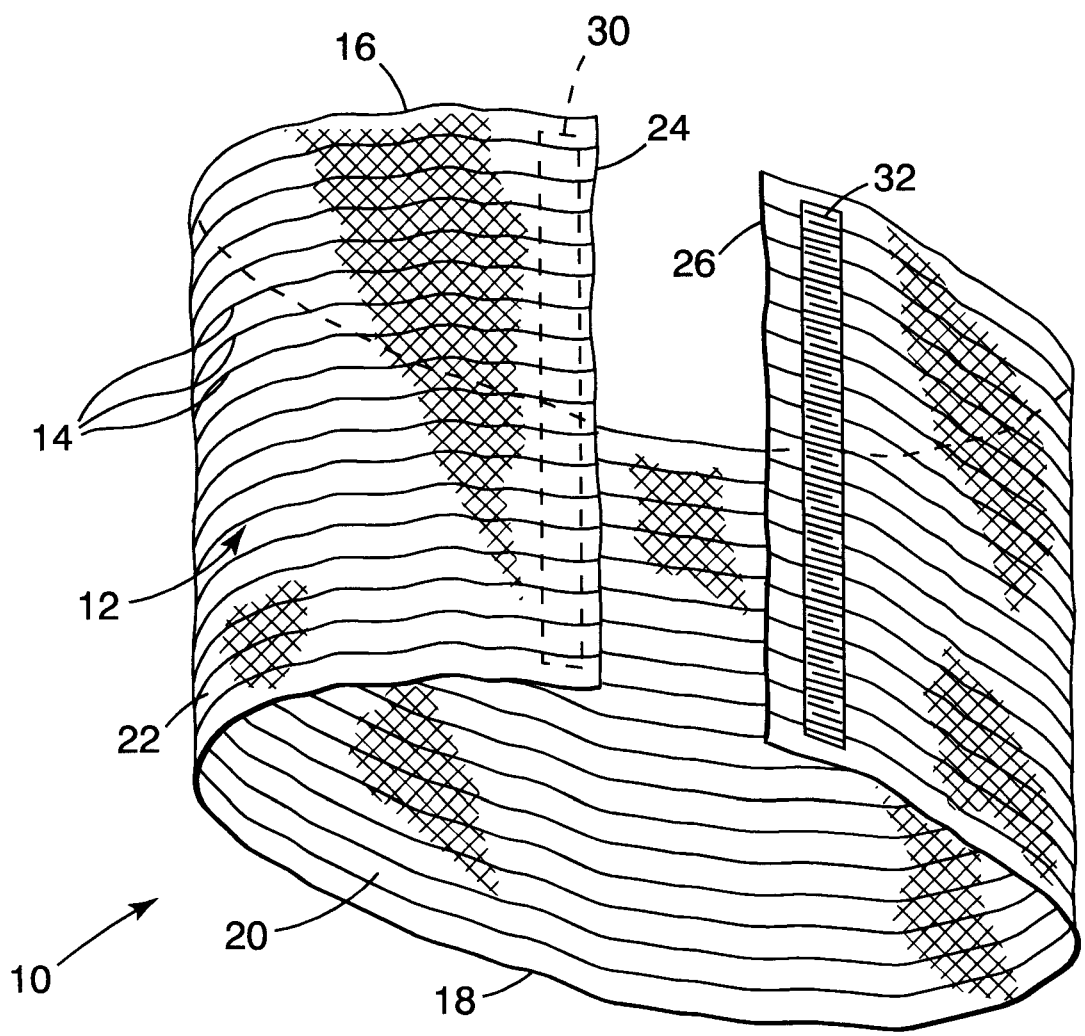
FIG. 1 is a perspective view of a surgical binder in accordance with the present invention.

A preferred embodiment of the surgical binder of the present invention is described with reference to FIGS. 1 and 2. Surgical binder 10 includes an elasticized main body portion 12 having a generally elongate rectangular shape when laid flat, as shown in FIG. 2. Although the elasticized main body portion 12 is shown as being generally rectangular in shape, it may be formed in a variety of other shapes, such as an elongated curved band. As long as it is configured to encircle the torso of a patient and is sufficient to cover the wound area and apply adequate pressure, the binder can be of a variety of shapes.

The elasticized main body portion 12 is made of a breathable material. At least a portion of the breathable material is elasticized using gathering, elastic stitching (often referred to as shirring). In FIGS. 1 and 2, this stitching is preferably in the form of a plurality of rows 14. The breathable material may or may not be elastic (i.e., stretchable) prior to being elasticized. Preferably, it is substantially nonelastic material prior to being elasticized. As used herein, "elasticizing" the material means that elasticity and stretchability are imparted to the material as a result of the gathers formed by the gathering, elastic stitching.

As used herein, a breathable material permits passage of air through it, such as from the atmosphere to the skin and wound area. As used herein, a substantially nonelastic material is one that does not stretch a significant amount beyond its normal (nonelasticized) size. That is, although there may be some small amount of stretch in the nonelastic material prior to it being elasticized, preferably it does not stretch, particularly in the longitudinal direction (of the main body portion). Such substantially nonelastic material is used in preferred embodiments of the surgical binder of the present invention.

A wide variety of materials can provide breathability. For example, cotton, gauze, flannel, muslin, polyester, and blends thereof can be used. Preferred fabrics are those that are washable. If desired, the fabrics chosen can have various prints or designs to provide an attractive nonmedical-looking binder. Various widths of fabric may be used, preferably the fabric is at least about 18–24 inches (about 45–61 centimeters) wide, such that the main body portion 12 can be made out of one length of fabric. It should be understood, however, that the main body portion 12 can include a plurality of panels of fabric sewn together.

A preferred embodiment of the elasticized main body portion 12 has a generally rectangular shape with two opposing edges 16 and 18 parallel to the longitudinal axis of the main body portion 12, an inner side 20, an outer side 22, and two opposing ends, shown as a first end 24 and a second end 26. Typically, the elasticized main body portion 12 is made from a single layer of material, although it may be preferable to use two or more layers of material in order to provide greater support. The different layers are typically arranged so that they overlap and are fastened together, e.g., by sewing, along their perimeters, thereby providing a lined main body portion, for example.

Regardless of the specific shape of the elasticized main body portion 12, its length (i.e., the dimension from the first end 24 to the second end 26) is less than the circumference of the patient's torso, but can be stretched to be equal to or greater than the circumference of the patient's torso. Preferably, the elasticized main body portion 12 can be stretched by at least about 30% of its length, and often by as much as about 100%. Thus, the length of the breathable material prior to being elasticized (and hence, gathered) is greater than the circumference of the patient's torso. The binder can be made in a variety of sizes (e.g., small, medium, large), each size accommodating a range of different chest dimensions. Typically, the length of the material after being elasticized is about 23 inches (58cm) for an extra small size, about 25 inches (64cm) for a small size, about 27 inches (69cm) for a medium size, and about 29 inches (74cm) for a large size.

The gathering, elastic stitching imparts stretchability to the main body portion 12 of surgical binder 10. Thus, the main body portion becomes elasticized such that it is stretchable and conformable to the torso of the patient. This enables easy adjustment of the binder to properly fit around the patient's torso and ensures that gentle but firm pressure is applied. Significantly, this method of imparting elasticity or stretchability to the binder allows for the application of gentle pressure that typically does not restrict a patient's respiration.

Figure 2:
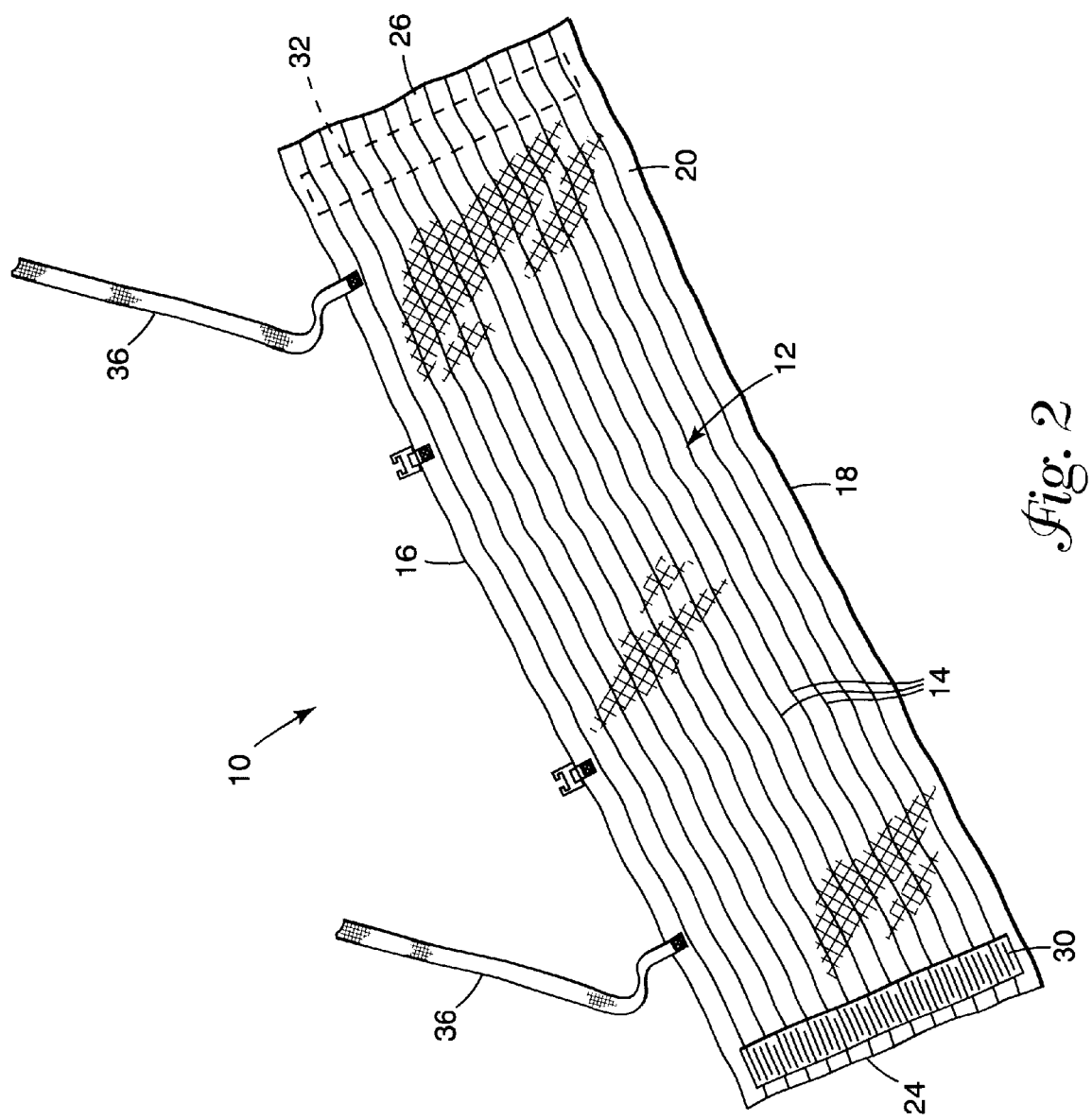
FIG. 2 is a plan view of a surgical binder in accordance with the present invention when the binder is not in use and is laid flat with the inner side facing upward.

In the preferred embodiments shown in FIGS. 1 and 2, a plurality of rows 14 of gathering, elastic stitching, which are each shown to be continuous, are generally parallel to the opposing edges 16 and 18 and generally equally spaced apart (e.g., about 1 cm apart). This configuration is not a necessary requirement, as long as the main body portion 12 can be stretched to conform to a patient's torso. Preferably, the stitching allows for the main body portion 12 to be stretched and returned substantially (and often completely) to its original shape under the recovery force of the elastic stitching after being stretched. Thus, the gathering, elastic stitching can be in the form of intersecting rows, random stitching forming lines of loops, circles, and the like, or a regular array of stitching in the form of various shapes. The lines or rows of stitching may be continuous or discontinuous, and may be formed from a variety of lengths of stitches. In particularly preferred embodiments, the elasticized main body portion 12 has gathering, elastic stitching substantially uniformly distributed over the entire surface of the material forming the main body portion 12. It should be understood however, that only a portion (e.g., at least about 50%) of the main body portion need to include gathering, elastic stitching for sufficient stretch. This elasticized stitching (shirring) can be imparted to the breathable material using well known techniques. As an example of how random shirring is applied to fabric, see Ruddy, *American Sewing Guild Notions,* January 1997.

Surgical binder 10 is positioned on a patient's torso so that it closes at the front, back, or side of the patient's torso, although it can close at other locations on the patient's body. The fastening system used to form the closure preferably includes a hook and loop fastener such as that available under the trademark VELCRO. Alternatively, or additionally, other conventional fasteners may also be used, such as snaps, tabs, ties, zippers, hook-and-eyes, etc. The fastening system is preferably attached at the ends of the main body portion. For example, as shown in FIG. 2, which is a plan view of the binder laid open with the inner side 20 facing upward, a strip of hook material 30, preferably about 3–4 centimeters wide, is provided at the first end 24 along the height of the inner side 20 of the elasticized main body portion 12 and a strip of loop material 32, preferably about 3–4 centimeters wide, is provided at the second end 26 on the outer side 22 of the elasticized main body portion 12.

Although FIGS. 1 and 2 show a preferred configuration of a hook and loop fastener, the hook and loop material may be cut in other configurations. For example, on the inner side 20 of the elasticized main body portion 12 at the first end 24 can be provided one or more horizontal strips or tabs of hook material positioned vertically that cooperate with the loop material 32 to secure the binder 10 closed. As another example, a strip of loop material, preferably about 3–4 centimeters wide, may be provided along the height of the inner side 20 of the elasticized main body portion 12 at the first end 24. On the outer side 22 of the elasticized main body portion 12 at the second end 24 may be provided two or more spaced apart strips of hook material, preferably about 3–4 centimeters wide, running along the height of the elasticized main body portion 12.

Referring to FIG. 2, optionally, the surgical binder 10 may further be provided with at least one strap, and preferably, a pair of conventional adjustable shoulder straps 36 as is well known in the art. If one strap is used, it can be attached at the front of the main body portion 12 ("front" being defined when positioned on a patient) and positioned around the back of the neck of the patient. In a preferred embodiment, the straps 36 are attached at the upper edge 16 of the elasticized main body portion 12.

To apply surgical binder 10, a patient or healthcare provider arranges the binder 10 so the first and second ends 24 and 26 of the binder overlap and are located at a desired location on the body. If the binder is provided with shoulder straps 36, the straps 36 are placed over the shoulders. A patient should be able to apply the binder without assistance and with minimal pain or discomfort. Furthermore, once the binder is applied, it is relatively comfortable.

The complete disclosures of the patents, patent documents, and publications cited herein are incorporated by reference in their entirety as if each were individually incorporated. Various modifications and alterations to this invention will become apparent to those skilled in the art without departing from the scope and spirit of this invention. It should be understood that this invention is not intended to be unduly limited by the illustrative embodiments and examples set forth herein and that such examples and embodiments are presented by way of example only with the scope of the invention intended to be limited only by the claims set forth herein as follows.

What is claimed is:

1. A surgical binder comprising:
    a main body portion comprising material having a plurality of rows of gathering, elastic stitching extending substantially throughout the entire length and width of the main body portion for application of evenly distributed pressure to a patient; wherein the elasticized main body portion is elongated with an inner side, an outer side, two opposing edges, and two opposing ends; and
    a fastener system attached to the two opposing ends of the main body portion.

2. The surgical binder of claim 1 wherein the material is breathable.

3. The surgical binder of claim 2 wherein the breathable material is substantially nonelastic.

4. The surgical binder of claim 1 wherein the fastener system comprises a hook and loop fastener.

5. A surgical binder comprising:
    a main body portion comprising breathable material and a plurality of rows of gathering, elastic stitching substantially uniformly distributed therein; wherein the elasticized main body portion is elongated and generally rectangular in shape with an inner side, an outer side, two generally parallel opposing edges, and two generally parallel opposing ends; and further wherein the gathering, elastic stitching spans substantially the entire length and width of the elongated main body portion; and
    a fastener system comprising a hook and loop fastener attached to the two generally parallel opposing ends of the main body portion.

6. The surgical binder of claim 5 wherein the breathable material is substantially nonelastic.

7. A method of binding a patient after surgery comprising applying a surgical binder comprising:
    an elasticized main body portion configured to encircle a torso of a patient, the main body portion comprising breathable material and gathering, elastic stitching therein positioned for application of evenly distributed pressure to the torso of the patient for compression of a wound; and
    a fastener system attached to the main body portion.

8. A method of binding a patient after surgery comprising applying a surgical binder comprising:
    a main body portion comprising material having a plurality of rows of gathering, elastic stitching extending substantially throughout the entire length and width of the main body portion for application of evenly distributed pressure to a patient; wherein the elasticized main body portion is elongated with an inner side, an outer side, two opposing edges, and two opposing ends; and
    a fastener system attached to the two opposing ends of the main body portion.

9. A method of binding a patient after surgery comprising applying a surgical binder comprising:
    a main body portion comprising breathable material and a plurality of rows of gathering, elastic stitching substantially uniformly distributed therein; wherein the elasticized main body portion is elongated and generally rectangular in shape with an inner side, an outer side, two generally parallel opposing edges, and two generally parallel opposing ends; and further wherein the gathering, elastic stitching spans substantially the entire length and width of the elongated main body portion; and
    a fastener system comprising a hook and loop fastener attached to the two generally parallel opposing ends of the main body portion.

10. A surgical binder comprising:
    an elasticized main body portion configured to encircle a torso of a patient after surgery on one or both breasts, the main body portion comprising breathable material and gathering, elastic stitching therein positioned for application of evenly distributed pressure to the torso of the patient for securing a dressing in place over the surgical area; and
    a fastener system attached to the main body portion.

* * * * *